United States Patent [19]

VanEffen et al.

[11] 4,440,603
[45] Apr. 3, 1984

[54] APPARATUS AND METHOD FOR MEASURING DISSOLVED HALOGENS

[75] Inventors: Richard M. VanEffen; James D. McLean; Dalton L. Decker, all of Midland, Mich.

[73] Assignee: The Dow Chemical Company, Midland, Mich.

[21] Appl. No.: 389,360

[22] Filed: Jun. 17, 1982

[51] Int. Cl.³ ............................................. G01N 27/46
[52] U.S. Cl. .................................. 204/1 T; 204/290 F; 204/400
[58] Field of Search ............... 204/1 T, 1 B, 195 R, 204/195 M, 290 F, 400

[56] References Cited

U.S. PATENT DOCUMENTS

| | | | |
|---|---|---|---|
| 3,711,385 | 1/1973 | Beer | 204/59 |
| 3,778,307 | 12/1973 | Beer | 117/221 |
| 4,028,197 | 6/1977 | Capliano | 204/1 B |
| 4,214,971 | 7/1980 | Heikel et al. | 204/290 |
| 4,354,915 | 10/1982 | Stachurski et al. | 204/290 F |

Primary Examiner—T. Tung
Attorney, Agent, or Firm—Burke M. Halldorson

[57] ABSTRACT

Liquids are monitored for dissolved halogens using amperometric detection based on the use of halogen specific electrodes of a conductive substrate on which is formed an adherent surface film of $[Ti_x(Ru, Ir)_{1-x}]O_2$, wherein x=mole fraction $\geq 0$ to $< 1$, and (Ru, Ir) represents either ruthenium or iridium or mixtures thereof. The described electrodes resist corrosion and failure in extremely harsh environments, e.g., hot concentrated brine solutions.

14 Claims, 2 Drawing Figures

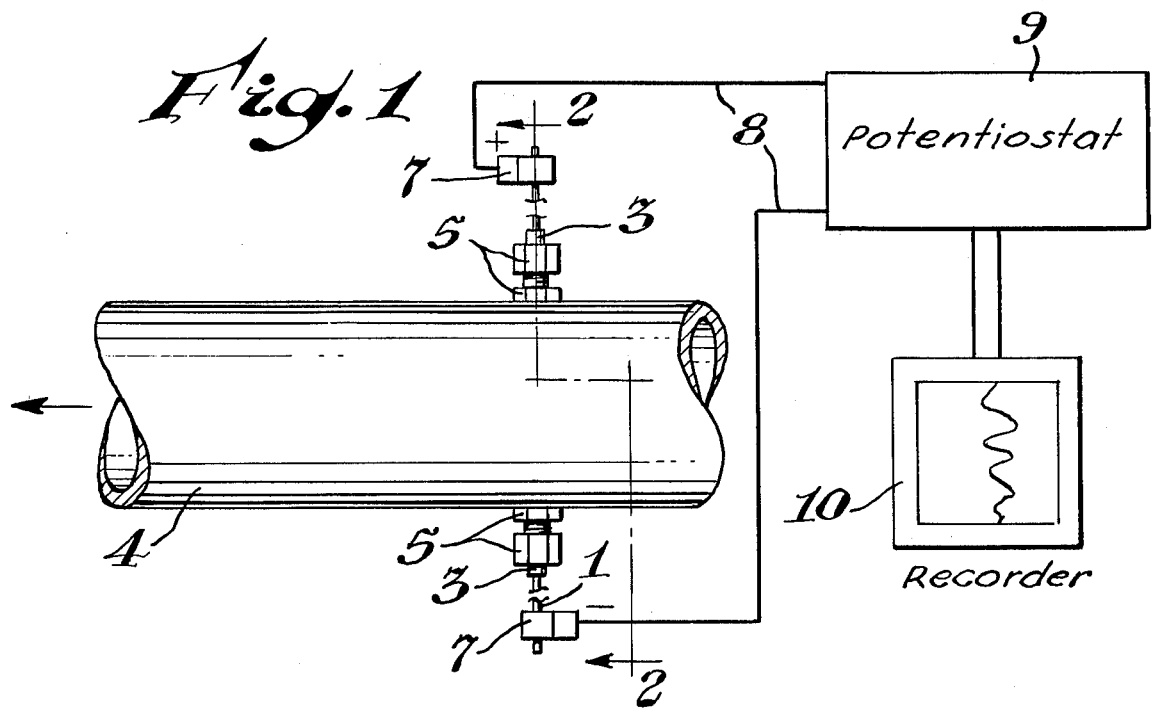
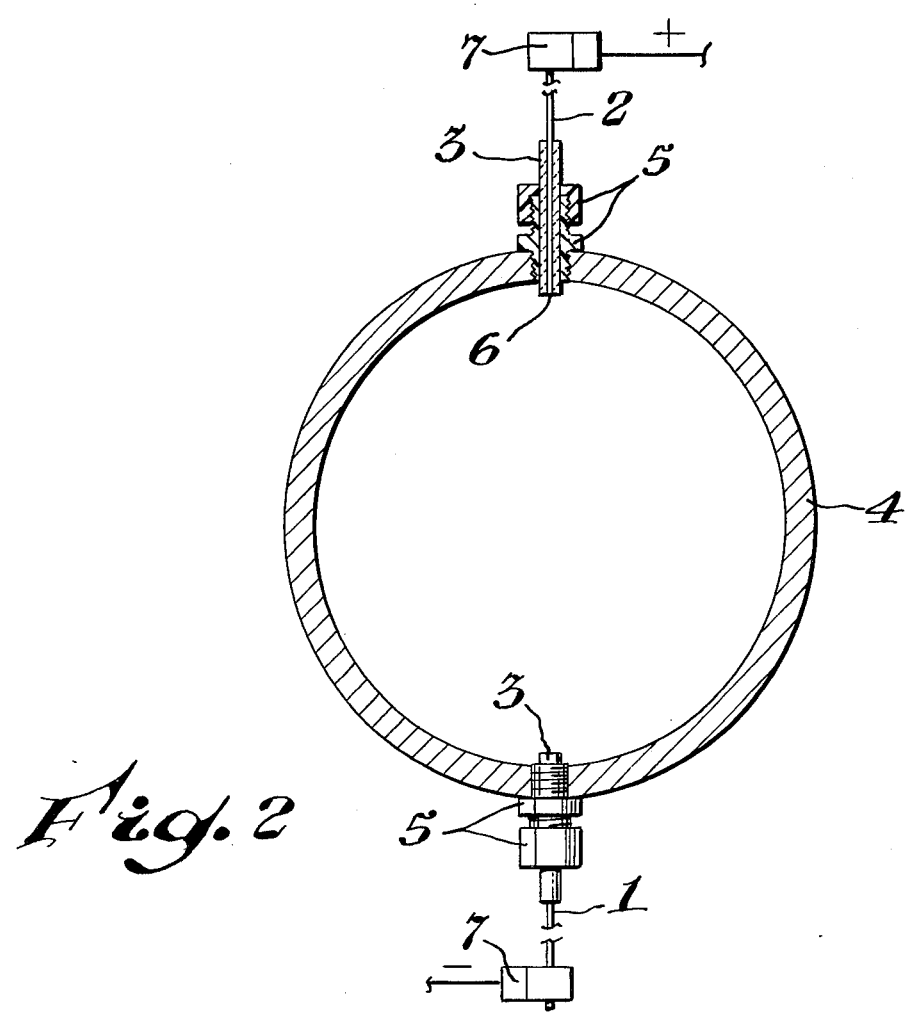

APPARATUS AND METHOD FOR MEASURING DISSOLVED HALOGENS

BACKGROUND OF THE INVENTION

Dissolved halogen detectors are primarily designed for the detection of chlorine, but will also respond to bromine and iodine. Two detection methods are generally used: potentiometric and amperometric. Potentiometric electrodes respond to total oxidizers and are based upon the development of a potential at an indicating or oxidation-reduction potential electrode which is usually constructed of platinum (OPR) electrode). Platinum ORP electrodes have been used in combination with a reference electrode in certain harsh chemical environments, e.g., hot brine streams, but have been prone to early failure due to corrosion and fouling.

Amperometric halogen electrodes are based upon the principle that halogens are easily reduced when the proper potential is applied to an electrode. A current will flow which is proportional to the concentration of the halogen. Two electrodes are required, one being the cathode (working) electrode, often of platinum, at which the halogen is reduced, and the other being the anode (counter) electrode at which some other reaction occurs to provide the necessary current flow. Premature electrode corrosion and fouling occur with amperometric electrodes, similarly as with the described platinum ORP electrodes.

SUMMARY OF THE INVENTION

The invention concerns apparatus and method for the detection of dissolved halogens using amperometric halogen responsive electrodes which are corrosion and fouling resistant.

More specifically, the apparatus of the invention comprises a halogen specific detector for the amperometric measurement of dissolved halogen gases and chemical analogs thereof in a stirred or flowing liquid electrolyte solution, the detector comprising a cathode electrode and at least a second electrode which is a reference electrode, the cathode electrode comprising a substrate of an inert and electrically conductive material on which is formed a surface film layer which is electrically conductive and of a composition which comprises $[Ti_x(Ru, Ir)_{1-x}]O_2$, wherein x=mole fraction $\geq 0$ to $<1$, and (Ru, Ir) represents either ruthenium or iridium or mixtures thereof, the apparatus including a potentiostat means for maintaining a constant or pulsed D.C. negative voltage on the cathode electrode vs. the reference electrode in the range between about $-0.1$ to $-1$ volt, and electronic readout means for displaying a readable signal which is proportional to the current produced as a result of the applied voltage.

A further aspect of the invention is the amperometric method for measuring dissolved halogen gases and their chemical analogs in a stirred or flowing electrolyte solution, and which comprises contacting the solution to be measured with a cathode electrode and at least a second electrode which is a reference electrode, the cathode electrode comprising a substrate on which is formed an adherent electrically conductive film, and which forms the working surface of the cathode electrode, the film being of a composition which comprises $[Ti_x(Ru, IR)_{1-x}]O_2$, wherein x=mole fraction $\geq 0$ to $<1$, and (Ru, Ir) represents either ruthenium or iridium or mixtures thereof, impressing a negative constant or pulsed D.C. voltage on the cathode electrode whereby the cathode electrode has a negative polarity of between about $-0.1$ to $-1$ volt, and which avoids substantial reductions of other electroactive materials in the solution other than said halogen analytes of interest, and measuring the current as a result of the applied voltage to quantitate responding halogen analyte(s) of the solution.

The apparatus and method described respond to all three halogen forms in aqueous solution and chemical analogs thereof, specifically the analogs: hypochlorite, hypochlorous acid, hypobromite, hypobromous acid, and hypoiodous acid. The electrodes may be further applied to the detection of dissolved halogens in nonaqueous polar solvents such as alcohols, provided sufficient electrolyte solute is present other than halogen analyte, in order to permit amperometric detection. Typically, this requires the electrolyte solute to exceed the analyte solute by approximately a ratio of 10:1; and in this respect the invention operates under the same limiting parameters as prior amperometric electrodes and methods.

A further advance permitted by the invention is the two-electrode form of apparatus described as the preferred apparatus, and in which the anode electrode serves as a reference electrode or what is more aptly described as a "pseudo-reference" electrode. Anode electrodes of the composition of the cathode electrode form an unusually stable "pseudo-reference" electrode which is especially useful for halogens analysis in harsh environments where standard reference electrodes would not be suitable, or would lead to early corrosion related failures.

THE DRAWING

Yet further objects and advantages of the invention will, in part, be pointed out and, in part, be apparent from the following detailed description taken together with the accompanying Drawing in which:

FIG. 1 is an elevational view showing a section of conduit which is associated, e.g., with a chemical process or plant, and shows additionally, the apparatus of the invention as employed as a process monitor for measuring dissolved halogens in the liquid flowing in such conduit; and FIG. 2 is a cross-sectional view taken along reference line 2—2 of FIG. 1.

DETAILED DESCRIPTION OF THE INVENTION

Referring now to the Drawing, a preferred embodiment of a halogen specific detector comprises two electrodes, a cathode electrode 1, and an anode electrode 2, the latter which is also described as a reference or "pseudo reference" electrode according to the teachings hereof. The electrodes of the illustrated embodiment are identically constructed, each consisting of the electrode itself in the geometric form of a metal rod or cylinder which is encapsulated in an insulator, preferably a glass filled Teflon ® sleeve or jacket element 3. For purposes of mounting the electrodes in a conduit 4, e.g., for monitoring dissolved halogens flowing in a chemical process stream, the sheathed or jacketed electrodes are pressure fitted in the bores of two-element fluorocarbon resin plastic fittings 5 obtained commercially from Fluoroware, Inc., and described in U.S. Pat. No. 3,977,708. The fluorocarbon fittings are threadably fastened in conduit 4 with only the circular end face 6 of each electrode being exposed within conduit 4, and which exposed end face forms the active or working portion or area of the electrode.

The opposite ends of electrodes 1, 2 are attached, e.g., to alligator clamps 7, and through electrical leads 8 to a potentiostat means 9. The potentiostat means 9 impresses or maintains a constant negative D.C. voltage or negative pulsed D.C. voltage on the cathode electrode vs. the anode (reference) electrode irrespective of the current flowing through the electrodes. The potentiostat means also contains terminals which output the current through the cathode which is the result of the impressed voltage; and the value of which is displayed or retrievably recorded, e.g., by a strip chart recorder 10. The potentiostat means 9 and recorder 10 are components used in prior amperometric detectors, and no improvements to these have been invented herein per se; the applicants relying on the Doctrine of Equivalents by which comparable electronics and readout hardware may be selected for use in the inventive apparatus and method.

The essential feature of the invention is the materials of construction of electrodes 1, 2 (and not their geometry or size which may be varied). More specifically, electrodes 1, 2 are each constructed of an electrically conductive core or substrate having adhered thereto, and forming the active portion of the electrode, a surface film of one or plural coatings. The surface film composition is essentially $[Ti_x(Ru, Ir)_{1-x}]O_2$ wherein x=mole fraction $\geq 0$ to $<1$; and (Ru, Ir) represents ruthenium or iridium or mixtures thereof. The film may contain other components and will generally be found to contain, e.g., some chlorides which are unreacted residues of precursors used in the manufacturing process to produce the characterized film. These residues and other components may be present so long as they do not detrimentally affect the halogen specific detection properties of the electrodes, or their inertness to the liquid chemical being analyzed.

The most preferred forms of the invention use an inert substrate of titanium; and as the film, a composition of $(Ti_xRu_{1-x})O_2$ solid solution; wherein x=mole fraction $>0$ to $<1$. Sufficient ruthenium is present in this preferred material to produce electrical conductivity; whereas sufficient titanium is present to avoid corrosion when subjected to hot oxidizing brine solution, (e.g., concentrated NaCl brine at 100° C.).

Alternative substrates for electrodes 1, 2 may be selected, e.g., from the various "valve" metals described in U.S. Pat. Nos. 3,778,307 and 4,214,971, and particularly such valve metals which would be self-healing in corrosive environments similar to the properties of titanium. The referenced patents are also incorporated herein for their teachings concerning the manufacture of electrodes having the surface film and substrate which the amperometric electrodes of this invention employ.

The preferred method of operation of the invention is now described.

A constant D.C. potential (on the order of 0.1-1.0 depending on the specific conditions) is applied to the two electrodes by the potentiostat means, with the working electrode having the negative polarity. The resulting current due to dissolved halogen analyte is measured by the potentiostat means and a signal proportional to the current is used to operate the strip chart recorder.

This measured current is proportional to e.g., dissolved halogen gas analyte reduced at the cathode electrode according to the equation:

$$X_2 + 2e^- \rightarrow 2X^- \text{ (X=any responding halogen gas analyte present)}$$

at the counter electrode, an oxidation reaction must occur to provide the necessary current for the working electrode. In a typical chloride brine system, the reaction at the anode is oxidation of chloride to chlorine $$2Cl^- \rightarrow Cl_2 + 2e^-.$$

The advantage of the described electrode material is that both halogen reduction and halide oxidation occur very easily compared to other electrode materials. Thus, a relatively small voltage is used for the amperometric determination, prolonging the life of the electrodes in harsh environments.

It is also mentioned that the invention is usually practiced observing the following parameters:

(1) Monitored solution should contain an excess of halide ions;

(2) Flow rate (or stirring rate) and pH of the solution should be constant;

(3) The solution is preferably homogeneous (as opposed to a slurry).

(4) The halogen concentration is between >5-20 ppm to weight percent.

(5) Potentiostat means is used for applying a constant (as opposed to a pulsed) D.C. voltage.

The extent to which condition (1) is obeyed generally determines the minimum active surface area required of the anode. That is, as the halide concentration becomes more dilute, the active anode surface needs to be correspondingly increased in order that the current density does not reach a level which can cause a detrimental voltage shift, and, hence, loss of functionality of the anode as a reference electrode or "pseudo-reference" electrode". The substitution of another material for the anode, e.g., platinum, will similarly require increased active electrode area to avoid detrimental voltage shifting, since platinum has been found to be inherently less suitable as a pseudo-reference electrode than those anode materials described for preferred use in this invention.

Conditions (2) and (3) can be adjusted for by calibration. In purely nonaqueous solutions, pH control is not of course, a meaningful response variant.

Condition (4) represents the current practical sensitivity limit of the invention, whereas condition (5) can be overcome provided a traditional three electrode system is used, using as a reference electrode, Ag/AgCl or the conventional fiber-tipped saturated calomel electrode (SCE). Otherwise, the inherently high capacitance of the two electrode system, especially with solid electrodes, tends to product high faradaic currents making the pulsed mode of amperometric detection undesirable.

EXAMPLE 1

This Example describes the detection of $Cl_2$ and $Cl_2$ analogs in a sample of heated, concentrated sodium chloride brine at a controlled pH of 5.5. The process in which the invention is applied involves the sparging of the brine with chlorine gas to oxidize organic impurities which are converted to $CO_2$ and removed. The detector used in this study is the two electrode design illustrated in the Drawing. The cathode comprises a titanium substrate, having as the film composition $[Ti_xRu_{1-x}]O_2$ solid solution, where x=mole fraction 0.7 to 0.9. The electrodes are inserted in the process conduit at diametrically opposite points, and are spaced apart by about 4-6". Each electrode is 3/32" in diameter, and the applied potential, $E_{ap}=-0.5$ V. The electrodes are daily evaluated and found to perform satisfactorily in this harsh environment to detect chlorine concentrations varying from about 100 to 500 ppm. Occasionally, excursions of pH to highly acidic values are found to increase the response by a factor of about 2, with the electrodes gradually returning to calibrated responses after about two days. Allowing the electrodes to stand in static solution is observed to oppositely cause a decrease in response by a factor of about 2; but with electrode response also returning to normal within a period of about two days after flow is resumed.

EXAMPLE 2

In this Example, dissolved chlorine is measured in a pH 1.02 concentrated sodium chloride brine. At this pH, free $Cl_2$ is the predominating form of the halogen. This experiment uses a working electrode consisting of a 3/32" diameter rod of titanium, and as the film, $(Ti_xRu_{1-x})O_2$, x=mole fraction 0.7 to 0.9. A similar electrode is used as the reference electrode. The solution is kept flowing by means of a magnetic stirrer, and the applied potential to the working electrode is $-0.6$ V versus the reference electrode. Dissolved chlorine is successfully measured over the broad range of 10-640 ppm in this difficult sample matrix.

EXAMPLE 3

This example describes the detection of dissolved bromine in a mixed organic solvent/water matrix. The detector uses a cathode electrode as described in Example 2; and which is used in combination with an anode-reference electrode comprising approximately 6 inches of coiling #18 gauge platinum wire. The pH in this system is not defined because the solvent is primarily organic in composition and the predominating form of the bromine is as free $Br_2$. The dissolved bromine is successfully determined in this matrix over the broad range of 0.1 to 5.0 percent w/w using $E_{ap}=-0.5$ V for this determination.

EXAMPLE 4

Iodine determination is described in this example. A solution containing 10 percent HI and 6 percent $H_2SO_4$ in water is used as the test matrix. Twenty-five cc of this solution is placed in a glass cell whose headspace is kept purged with nitrogen to prevent air oxidation of the HI. The solution is stirred at a constant rate to simulate a flowing stream, and two amperometric electrodes are inserted. A D.C. potential of $-0.2$ V is applied across the two electrodes. After allowing an hour for the electrodes to adjust to the matrix (a large initial background current occurred which decayed away in that period of time), aliquots of iodine standard are added corresponding to successive increases of 18 ppm iodine in the matrix. The resulting current is observed to be linear with the concentration of dissolved iodine in the range of 18-340 ppm. The estimated detection limit is about 5 ppm dissolved iodine.

What is claimed is:

1. Apparatus comprising a halogen specific detector for the amperometric measurement of dissolved halogen gases and chemical analogs thereof in a stirred or flowing liquid electrolyte solution, the detector comprising a cathode electrode and at least a second electrode which is a reference electrode, the cathode electrode comprising a substrate of an inert and electrically conductive material on which is formed an adherent surface film which is electrically conductive and of a composition which comprises $[Ti_x(Ru, IR)_{1-x}]O_2$, wherein x=mole fraction $\geq 0$ to $<1$, and (Ru, Ir) represents either ruthenium or iridium or mixtures thereof, the apparatus including potentiostat means for impressing a constant or pulsed D.C. negative voltage on the cathode electrode vs. the reference electrode in the range between about $-0.1$ to $-1$ volt, and electronic readout means for displaying a readable signal which is proportional to the current produced as a result of the applied voltage.

2. The apparatus of claim 1 wherein the film composition of the cathode comprises $(Ti_xRu_{1-x})O_2$ solid solution.

3. The apparatus of claim 2 wherein the substrate of the cathode electrode comprises titanium metal.

4. The apparatus of claim 2 wherein the reference is an anode electrode.

5. The apparatus of claim 4 wherein the anode electrode comprises a substrate of an inert and electrically conductive material on which is formed an adherent surface film which is electrically conductive and of a composition which comprises $[Ti_x(Ru, Ir)_{1-x}])O_2$, where x=mole fraction $\geq 0$ to $<1$, and (RU, Ir) represents either ruthenium or iridium or mixtures thereof.

6. The apparatus of claim 5 wherein the film composition of the anode and cathode electrodes, respectively, consists essentially of $(Ti_xRu_{1-x})O_2$ solid solution and the substrates thereof consist essentially of titanium metal.

7. The apparatus of claim 6 which uses a potentiostat means for maintaining a constant D.C. negative voltage on the cathode electrode vs. the reference anode electrode.

8. Amperometric method for measuring dissolved halogen gases and chemical analogs thereof in a stirred or flowing electrolyte solution, and which comprises contacting the solution to be measured with a cathode electrode and at least a second electrode which is a reference electrode, the cathode electrode comprising a substrate on which is formed an adherent electrically conductive film, and which forms the working surface of the cathode electrode, the film being of a composition which comprises $[Ti_x(Ru, Ir)_{1-x}]O_2$, wherein x=mole fraction $\geq 0$ to $<1$, and (Ru, Ir) represents either ruthenium or iridium or mixtures thereof, impressing a negative D.C. voltage on the cathode electrode whereby the cathode electrode has a negative polarity of between about $-0.1$ to $-1$ volt, and which avoids substantial reductions of electroactive materials in the solution other than said halogen analytes of interest, and measuring the current flowing as a result of the applied voltage to measure responding halogen analyte(s) of the solution.

9. The method of claim 8 wherein the film composition of the cathode comprises $(Ti_xRu_{1-x})O_2$ solid solution.

10. The method of claim 9 wherein the substrate of the cathode electrode comprises titanium metal.

11. The method of claim 9 wherein the reference electrode is an anode electrode.

12. The method of claim 11 wherein the anode electrode comprises a substrate of an inert and electrically conductive material on which is formed an adherent surface film which is electrically conductive and of a composition which comprises $[Ti_x(Ru, Ir)_{1-x}]O_2$, where x = mole fraction $\geq 0$ to $<1$, and (Ru, Ir) represents either ruthenium or iridium or mixtures thereof.

13. The method of claim 12 wherein the film composition of the anode and cathode electrodes, respectively, consists essentially of $(Ti_xRu_{1-x})O_2$ solid solution and the substances thereof consist essentially of titanium metal.

14. The method of claim 13 which comprises the step of impressing a constant D.C. negative voltage on the cathode electrode vs. the reference anode electrode.

* * * * *